United States Patent [19]

Morawsky et al.

[11] Patent Number: 5,736,125
[45] Date of Patent: Apr. 7, 1998

[54] COMPOSITIONS CONTAINING COPOLYMERS AS A THICKENING AGENT

[75] Inventors: Natalie A. Morawsky, Kingston, Great Britain; Gary T. Martino, Plainsboro, N.J.

[73] Assignee: National Starch and Chemical Investment Holding Corporation, Wilmington, Del.

[21] Appl. No.: 780,951

[22] Filed: Jan. 10, 1997

[51] Int. Cl.$^6$ .................................................. A61K 7/42
[52] U.S. Cl. ...................... 424/59; 424/60; 514/772.1; 514/772.4; 514/844; 514/847; 514/938
[58] Field of Search .................. 514/772.1, 772.4, 514/844, 847, 938; 424/59, 60

[56] References Cited

U.S. PATENT DOCUMENTS 5,156,911  10/1992  Stewart .................................. 428/355
5,318,995  6/1994  Mondet et al. ........................ 514/772.1
5,639,448  6/1997  Galleguillos et al. ............... 424/70.11

FOREIGN PATENT DOCUMENTS 0 550 745 B1  9/1995  European Pat. Off. .......... A61K 7/48

Primary Examiner—Terressa Mosley
Attorney, Agent, or Firm—Karen G. Kaiser

[57] ABSTRACT

The present invention is directed to compositions, particularly cosmetic compositions, in which the oil is thickened using at least one copolymer which has a hydrophobic functionality sufficient to provide at least partial solubility and optionally stability in oil and a hydrophilic functionality sufficient to provide thickening of the oil. Use of such copolymers as thickening agents are advantageous in that they are soluble and stable in the oil phase. Further, sufficient thickening may be accomplished using very low amounts of these copolymers without the use of additional polymeric thickeners.

15 Claims, No Drawings

COMPOSITIONS CONTAINING COPOLYMERS AS A THICKENING AGENT

BACKGROUND OF THE INVENTION

The present invention relates to compositions in which the oil is thickened using copolymers which have a hydrophobic functionality sufficient to provide at least partial solubility and optionally stability in oil and a hydrophilic functionality sufficient to provide thickening of the oil.

Numerous cosmetic compositions use oils as a primary component. Oils possess highly desirable cosmetic characteristics, such as cleansing, make-up removal, and emolliency. Unfortunately, their use is inconvenient in the fluid form and their application unpleasant and difficult.

These disadvantages are reduced by using the oil in the form of a thickened composition, such as a cream or a gel or in the form of an emulsion, particularly of the water-in-oil type. Preparation of such water-in-oil type emulsions requires thickening of the continuous oily phase of the emulsion. Thickening of the oily phase is also necessary to prepare such cosmetic gels, particularly anhydrous gels. The formulation in the form of an anhydrous gel is useful, especially if the substances present in the composition are sensitive to moisture and/or to oxygen.

Thickening of oils has been accomplished by incorporation of silicas, bentonites or metal salts of fatty acids such as aluminum salts, or esterified derivatives of sugars such as dextrin palmitate.

Such thickening has also been accomplished by incorporation of a wax in the oily phase. However, creams thickened with waxes have a feel or touch which is generally considered undesirable.

U.S. Pat. No. 5,318,995 to L'Oreal discloses thickening a water-in-oil type emulsion with certain copolymers containing a slight amount of ionic or ionizable groups. These copolymers are primarily of the formula

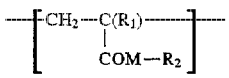

wherein M is O or $-N(R_3)-$; $R_1$ is H or $-CH_3$; $R_2$ is a $C_{4-22}$ hydrocarbon chain; $R_3$ is H or a $C_{1-22}$ hydrocarbon chain.

EP 550 745 to L'Oreal discloses thickening of the oil phase of a cosmetic composition using a combination of a first copolymer containing units derived from a lipophilic monomer and a hydrophilic monomer containing carboxylic or sulfonic acid groups which included copolymers such as those disclosed in U.S. Pat. No. 5,318,995 and a second copolymer containing units derived from a lipophilic monomer and a hydrophilic monomer containing an amine, amide, alcohol or ether group. Both copolymers are necessary to thicken the cosmetic composition.

Surprisingly, it has now been discovered that the oil phase of a composition may be thickened by incorporating as the sole polymeric thickener at least one copolymer which has a hydrophobic functionality sufficient to provide at least partial solubility and optionally stability in oil and a hydrophilic functionality sufficient to provide thickening of the oil.

SUMMARY OF THE INVENTION

The present invention relates to compositions, particularly cosmetic compositions, in which the oil is thickened using at least one copolymer which has a hydrophobic functionality sufficient to provide at least partial solubility and optionally stability in oil and a hydrophilic functionality sufficient to provide thickening of the oil. It is further directed to the process of preparing such compositions.

An object of the present invention is to provide a composition in which the oil is thickened using at least one copolymer which has a hydrophobic functionality sufficient to provide at least partial solubility and optionally stability in oil and a hydrophilic functionality sufficient to provide thickening of the oil.

Another object of the present invention is to provide a composition, particularly in the form of a cream, a gel, or an emulsion, more particularly a water-in-oil emulsion, in which the oil is thickened using at least one copolymer which has a hydrophobic functionality sufficient to provide at least partial solubility and optionally stability in oil and a hydrophilic functionality sufficient to provide thickening of the oil.

Still another object of the present invention is to provide a composition, particularly in the form of a cream, a gel, or an emulsion, more particularly a water-in-oil emulsion, in which the oil is thickened using at least one copolymer of $C_{12}$–$C_{22}$ acrylate or methacrylate.

A further object of the present invention is to provide a method of thickening oil using at least one copolymer which has a hydrophobic functionality sufficient to provide at least partial solubility and optionally stability in oil and a hydrophilic functionality sufficient to provide thickening of the oil.

These and other objects of the present invention will become apparent to one skilled in the art from the following detailed description and examples below.

DETAILED DESCRIPTION OF THE INVENTION

The present invention is directed to compositions, particularly cosmetic compositions, in which the oil is thickened using at least one copolymer which has a hydrophobic functionality sufficient to provide at least partial solubility and optionally stability in oil and a hydrophilic functionality sufficient to provide thickening of the oil. Use of such copolymers as thickening agents are advantageous in that they are soluble and stable in the oil phase. Further, sufficient thickening may be accomplished using very low amounts of these copolymers without the use of additional polymeric thickeners.

The hydrophobic functionality is necessary to provide at least partial solubility and preferably stability in oil. The hydrophobic functionality may be provided by any hydrophobic constituent conventionally used in the art including $C_{10}$–$C_{22}$ acrylates or methacrylates, $C_{10}$–$C_{22}$ acrylamides or methacrylamides, $C_{10}$–$C_{22}$ vinyl ethers or esters, siloxanes or $C_{10}$–$C_{22}$ alpha olefins; fluorinated aliphatic side-chains of at least 6 carbons; and alkyl styrene side-chains wherein the alkyl is of 1 to 24 carbon atoms. Of particular use in the instant invention are $C_{12}$–$C_{22}$ acrylates or methacrylates and styrenes, more particularly $C_{18}$–$C_{22}$ acrylates or methacrylates.

The hydrophobic functionality generally comprise from about 80% to about 98%, particularly from about 85% to about 97% by weight of the copolymer.

The hydrophilic functionality is necessary to thicken the oil and may be provided by of $C_3$–$C_6$ $\alpha,\beta$-ethylenically unsaturated carboxylic monoacid, $C_4$–$C_6$-unsaturated carboxylic diacid, and or monoester or monoamide of such carboxylic diacid. The unsaturated carboxylic monoacids include acrylic acid, methacrylic acid, and crotonic acid. The unsaturated carboxylic diacids include maleic acid and itaconic acid. The monoesters and monoamides are derived from alcohols or amines containing from 1 to 22 carbon atoms, respectively. Of particular use in the instant invention are acrylic acid and methacrylic acid.

Copolymers which have an acidity from about 0.1 to about 4.0 meq/g, particularly from about 0.4 to about 2.0 meq/g, are of use in this application. Copolymers with a molecular weight greater than 50,000, particularly in the range of about 50,000–200,000 daltons are also of use in this application.

Any one of the copolymers described above, or a blend of at least two, may be used in the instant invention. Those copolymers of alkyl acrylate or methacrylate and acrylic acid or methacrylic acid are particularly useful in the instant invention, more particularly docosyl ($C_{22}$) acrylate/styrene/acrylic acid and stearyl acrylate/methacrylic acid.

In the compositions, the amount of thickening copolymer, as defined above, is present in an amount sufficient to thicken the composition to the desired thickness. In general, it is present in an amount of from about 0.1% to about 12%, particularly from about 0.5 to about 10% by weight of the oil. If the composition is a neat composition, the thickening copolymer is present in an amount particularly from about 2 to about 8% by weight of the oil. Neat composition, as used herein, is intended to mean a composition which is essentially free of water. If the composition is an emulsion composition, the thickening copolymer is present in an mount particularly from about 0.5 to about 3.5% by weight of the oil. The composition may be thickened to the desired viscosity which is dependent upon the functional properties of the composition.

To thicken the oil phase, the copolymer is generally heated to above its melting point in the oil so as to allow it to more readily solubilize. Often, agitation is provided to further facilitate solubilization.

The oily phase is constituted by any oil or mixtures of oils conventionally employed in formulations and known in the art. The oils include, but are not limited to:

hydrocarbons, including the mineral oils, such as the paraffin oils, the vaseline oils, hydrogenated polyisobutylene, such as that commercially available from the firm of NIPPON OIL under the trademark PARLEAM, the branched hydrocarbons, such as those commercially available under the name ISOPAR;

the triglycerides, especially the vegetable oils, such as sunflower seed oil, sesame seed oil, rapeseed oil, sweet almond oil, calophyllum oil, palm oil, avocado oil, jojoba oil, olive oil, castor oil, or the grain germ oils, such as wheat germ oil;

various oily esters derived from a long-chain acid and/or alcohol, such as purcellin oil, isopropyl, butyl or cetyl myristate, isopropyl, butyl or ethyl-2-hexyl palmitate, isopropyl, butyl octyl, hexadecyl or isocetyl stearate, decyl oleate, hexyl laurate, propylene glycol dicaprylate, diisopropyl adipate, and the mixtures of $C_{12}$–$C_{15}$ benzoic esters commercially available under the tradename FINSOLV TN from the firm of WITCO;

the animal oils, such as perhydrosqualene;

the silicone oils, such as the dimethylpolysiloxanes, phenyldimethicones, cyclomethicones, and alkyldimethicones;

the long-chain alcohols, such as the oleyl, linoleyl, linolenyl, and isostearyl alcohols, or octyl dodecanol;

the esters derived from lanolic acid, such as isopropyl or isocetyl lanolate; and the acetyl glycerides, the octanoates and decanoates of alcohols, or of polyalcohols (especially of glycol or glycerol), and the ricinoleates of alcohols or of polyalcohols, e.g., cetyl ricinoleate.

In general, the instant copolymers are soluble in oils with the exception of certain silicone oils used alone. When the copolymer is not sufficiently soluble in oil, it may be possible to attain the desired viscosity as described above by using an organic cosolvent which is compatible with cosmetologic use. Representative cosolvents include, but are not limited to, ethanol, propanol, isopropanol, glycerol, and propylene glycol. The co-solvent is usually added directly to the oil and, in the case of an emulsion, before mixing with aqueous phase of the emulsion. Generally, the amount of co-solvent is not greater than 30 volume percent relative to the volume of the oil.

The instant copolymers can be used to thicken the oil in a composition of any form, including without limitation water-in-oil emulsions, oil-in-water emulsions, anhydrous compositions, and gelled oils.

The instant copolymers can be used to thicken compositions containing a water-in-oil type emulsion. When the instant copolymers are used in this type of system, a conventional emulsifying agent or surfactant may be added to provide a stable emulsion. Any emulsifying agent known in the art and compatible with cosmetologic usage may be employed in the instant invention. Such agents include, but are not limited to, glycerol isostearate such as IMITOR 780K (commercially available from Dynamit Nobel) and polyglycerol ethers having the formula:

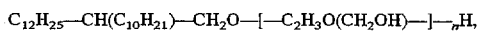

wherein n=an integer from 2 to 15 and described for example in French patent application 87.00 878 (2,593,509). The amount of the emulsifying agent is known in the art, but is generally in the range of up to about 15% by weight of the composition.

The instant copolymers may also be used to thicken compositions of the neat type; that is, those compositions which do not contain a substantial amount of water. Such neat compositions include, for example, creams and gels.

The compositions of the instant invention further may optionally contain a rheology control agent to improve the properties of the thickened oil composition if deemed necessary or desirable. This especially applies to the case in which the composition obtained is too viscous and tends to be brittle or is less viscous but not pliable enough and very fluid. These rheology control agents are known in the art and in general are nonionic amphophilic agents having an HLB value between about 12 and about 40. They are preferably used in the presence of water or a water-soluble alcohol. The rheological control agents include: the esters of fatty acids and polyoxyethylene sorbitan; the esters of fatty acids and polyoxyethylene glycerol; the esters of fatty acids and polyoxyethylenepropylene glycerol; the polyoxyethylene or polyoxypropylene alkyl ethers; the polyoxyethylene or polyoxypropylene alkyl phenyl ethers; and the polyoxyethylene Guerbet alcohols.

When the compositions of the instant invention are cosmetic compositions, they may optionally contain additives conventionally used in the cosmetic industry, including but not limited to active ingredients, perfumes, preservatives, and sunscreen agents. These additives and their use in cosmetic compositions are well known in the art and can be added by known techniques before, during, or after the thickening of the oil.

Various active lipophilic substances which are beneficial for the skin, such as tocopherol and its esters, the fatty esters of ascorbic acid, 18-β-glycyrrhetinic acid, the ceramides, screening substances absorbing ultraviolet light, antioxidants, etc., also may optionally be incorporated in the oils.

Cosmetic compositions, as used herein, is intended to include all oil-based cosmetic compositions, including, but not limited to, products for the care and hydration of the face and/or body, including the hands, pretanning lotions, sunscreens, sun tan lotions, after-sun lotions, make-up removers, lipsticks, mascaras, foundations, perfumed gels or oils, hair-treating oils, deodorants, bath oils, and cleansers.

The cosmetic compositions containing the thickened oil or water-in-oil emulsion have an agreeable appearance with a light texture. They are not significantly oily to the touch. Further, they penetrate the skin well and, upon application, leave a smooth, fresh sensation.

The following examples are presented to further illustrate and explain the present invention and should not be taken as limiting in any regard.

EXAMPLES

Example 1

A five percent solids solution of the copolymer in mineral oil (Drakeol 7 light mineral oil Penreco, Karns City, Pa.) was prepared and neutralized with 2-amino-2-methyl-1-propanol (AMP) (commercially available from Angus Chemical Co.) according to its acidity content. The sample was heated to 60° C. with constant agitation to allow the copolymer to solubilize. The solution was allowed to cool to room temperature overnight.

The above experiment was conducted individually using each of the copolymers listed in Table I.

TABLE I

| Copolymer | Appearance | Acidity (meq/g) | Molecular Weight (daltons) |
|---|---|---|---|
| 124-93 | solid | 0.45 | 116,000 |
| 124-130 | solid | 0.56 | 52,000 |
| 108-195 | solid | 0.56 | 188,000 |
| 124-194 | solid | 0.87 | 198,000 |
| 124-195 | solids | 1.16 | 60,000 |

Sample 124-93 is docosyl acrylate/styrene/acrylic acid in a ratio of 72/24/4 by weight.
Sample 124-130 is docosyl acrylate/styrene/acrylic acid in a ratio of 68/27/5 by weight.
Sample 108-195 is docosyl acrylate/styrene/acrylic acid in a ratio of 67/28/5 by weight.
Sample 124-194 is stearyl acrylate/methacrylic acid in a ratio of 92.5/7.5 by weight.
Sample 124-195 is stearyl acrylate/methacrylic acid in a ratio of 90/10 by weight.

All copolymers are available from the Landec Corporation, Menlo Park, Calif., USA. A control was prepared in which no copolymer was added.

The solubility and appearance of the resultant compositions were examined visually. The viscosity of the compositions were obtained using a Brookfield viscometer with Helipath spindles. The procedure recommended by Brookfield Engineering Laboratories, Inc. (Stoughton, Mass.) was used. The Spindle was set so that the crosspiece was covered by about ¼ inch of test material. Spindle TC was used for the more viscous compositions but did not provide a reading for the less viscous compositions. Spindle TE was used for the less viscous compositions, but did not provide a reading for the more viscous compositions. Spindle TA was used for the least viscous compositions. The results are listed in Table II.

TABLE II

| Co-polymer | Solubility | Appearance (initial) | Appearance (overnight) | Viscosity (Helipath) |
|---|---|---|---|---|
| Control | N/A | clear | clear | negligible |
| 124-93 | soluble | hazy | opaque | 300 cps spindle TA |
| 124-130 | soluble | hazy | opaque | 21,500 cps spindle TE |
| 108-195 | soluble | hazy | opaque | 15,500 cps spindle TE |
| 124-194 | soluble | hazy | opaque | 65,700 cps spindle TC |
| 124-195 | soluble | hazy | opaque | 20,200 cps spindle TC |

Each of the copolymers resulted in a stable formulation.

Example 2

| Ingredient | Amount (wt. %) |
|---|---|
| Sample 124-194 | 2.50 |
| Parsol 1789 | 1.25 |
| Isopropyl Myristate | 20.00 |
| Mineral Oil #7 | 76.25 |

Sample 124-194 is stearyl acrylate/methacrylic acid in a ratio of 92.5/7.5 by weight available from the Landec Corporation, Menlo Park, Calif., USA. Parsel 1789 is butyl methoxydibenzoylmethane commercially available from Givaudan-Roure in Clifton, N.J.

Drakeol Mineral Oil #7 is commercially available from Penreco, Karns City, Pa.

All ingredients were combined and heated to 80° C. The composition was mixed until uniform and then cooled to room temperature.

Viscosity of the resulting compositions were determined using the same procedure as in Example 1 using spindle TB and 10 rpm.

| Formulation | Viscosity |
|---|---|
| Experimental | 6,368 cps |
| Control | negligible |

Example 3

| Ingredient | Experimental Amount (wt. %) | Control Amount (wt. %) |
|---|---|---|
| Phase A | | |
| Dow Corning 344 | 5.0 | 5.0 |
| Abil EM 90 | 2.0 | 2.0 |
| Mineral Oil #7 | 8.5 | 8.5 |
| Octyl Stearate | 9.0 | 9.0 |
| Sample 124-194 | 1.0 | 0.0 |
| Phase B | | |
| Dionized H$_2$O | 73.80 | 74.80 |
| NaCl | 0.50 | 0.50 |
| Phase C | | |
| Liquapar | 0.20 | 0.20 |

Sample 124-194 is stearyl acrylate/methacrylic acid in a ratio of 92.5/7.5 by weight available from the Landec Corporation, Menlo Park, Calif., USA.

Dow Corning 344 is a silicone oil and is commercially available from Dow Corning, Midland, Mich.

Abil EM 90 is a silicone oil and is commercially available from Goldschmidt Hopewell, Va. Liquapar is isopropylparaben (and) isobutylparaben (and) butylparaben (preservative) and is commercially available from Sutton Labs, Chatham, N.J.

Procedure: Phase A was combined in a large vessel and heated to 80° C. Phase B was combined in a separate vessel. Slowly, with low agitation, Phase B was added to Phase A. Agitation was increased as an emulsion was formed and thickened so as to maintain uniform mixing. When the emulsion was uniform and at a temperature of 40° to 35° C., Phase C was added and mixed thoroughly.

Viscosity of the resulting compositions were determined using the same procedure as in Example 1 using spindle TB and 10 rpm.

| Formulation | Viscosity |
| --- | --- |
| Experimental | 24,520 cps |
| Control | 2,800 cps |

Example 4

| Ingredient | Experimental Amount (wt %) | Control Amount (wt %) |
| --- | --- | --- |
| Phase A | | |
| Mineral Oil #7 | 17.00 | 17.00 |
| Dioctyl Adipate | 2.00 | 2.00 |
| Estol 1526 | 3.00 | 3.00 |
| Myritol 318 | 5.00 | 5.00 |
| Arlacel p135 | 1.00 | 1.00 |
| Sample 124-194 | 1.00 | 0.00 |
| Phase B | | |
| Deionized $H_2O$ | 69.80 | 70.80 |
| Magnesium Sulfate (anhydrous) | 1.00 | 1.00 |
| Phase C | | |
| Liquapar | 0.20 | 0.20 |

Sample 124-194 is stearyl acrylate/methacrylic acid in a ratio of 92.5/7.5 by weight available from the Landec Corporation, Menlo Park, Calif., USA.

Estol 1526 is propyleneglycol dicaprylate/dicaprate and is commercially available from Unichema, Chicago, Ill.

Myritol 318 is caprylic/capric triglyceride and is commercially available from Henkel, Hoboken, N.J.

Arlacel p135 is PEG-30 dipolyhydroxystearate and is commercially available from ICI Surfactants, Wilmington, Del.

Liquapar is isopropylparaben (and) isobutylparaben (and) butylparaben (preservative) and is commercially available from Sutton Labs, Chatham N.J.

Procedure: Phase A was combined in a large vessel and heated to 80° C. Phase B was combined and heated to 40° C. Phase B was slowly added to Phase A with slow agitation and mixed thoroughly. The mixture was cooled to 40° to 35° C. and Phase C was added and mixed until uniform.

Viscosity of the resulting compositions were determined using the same procedure as in Example 1 using spindle TB and 10 rpm.

| Formulation | Viscosity |
| --- | --- |
| Experimental | 13,832 cps |
| Control | 200 cps |

We claim:

1. A composition comprising an oil and a polymeric thickener consisting essentially of at least one copolymer which has a hydrophobic functionality sufficient to provide at least partial solubility in oil and a hydrophilic functionality present in an amount effective to provide thickening of the oil, said hydrophilic functionality being provided by a constituent selected from the group consisting of $C_3$–$C_6$-α,β-ethylenically unsaturated carboxylic monoacid, $C_4$–$C_6$-α,β-ethylenically unsaturated carboxylic diacid, monoesters and monoamides of such carboxylic diacid.

2. The composition of claim 1, wherein the hydrophobic functionality is provided by a constituent selected from the group consisting of $C_{10}$–$C_{22}$-acrylate, $C_{10}$–$C_{22}$-methacrylate, $C_{10}$–$C_{22}$-acrylamide, $C_{10}$–$C_{22}$-methacrylamide, $C_{10}$–$C_{22}$-vinyl ether, $C_{10}$–$C_{22}$-vinyl ester, siloxane, $C_{10}$–$C_{22}$-alpha olefin, fluorinated aliphatic sidechain of at least 6 carbons, styrene, and $C_1$–$C_{24}$-alkyl-substituted styrene.

3. The composition of claim 2, wherein the hydrophobic functionality is provided by a constituent selected from the group consisting of $C_{12}$–$C_{22}$-acrylate, $C_{12}$–$C_{22}$-methacrylate, styrene, and $C_1$–$C_{24}$-alkyl-substituted styrene.

4. The composition of claim 1, wherein the hydrophilic functionality is provided by a constituent selected from the group consisting of acrylic acid and methacrylic acid.

5. The composition of claim 1, wherein the copolymer is selected from the group consisting of docosyl acrylate/styrene/acrylic acid and stearyl acrylate/methacrylic acid.

6. The composition of claim 1, wherein the copolymer is present in an amount ranging from about 0.1 to about 12% by weight of the oil.

7. The composition of claim 1, wherein the composition is neat and the copolymer is present in an amount of from about 2 to about 8% by weight of the oil.

8. The composition of claim 1, wherein the composition is a water-in-oil emulsion and the copolymer is present in an amount of from about 0.5 to about 3.5% by weight of the oil.

9. The composition of claim 1, wherein the composition is a cosmetic composition.

10. A process of thickening an oil comprising adding to the oil a polymeric thickener consisting essentially of at least one copolymer which has a hydrophobic functionality sufficient to provide at least partial solubility in oil and a hydrophilic functionality present in an amount effective to provide thickening of the oil, said hydrophilic functionality being provided by a constituent selected from the group consisting of $C_3$–$C_6$-α,β-ethylenically unsaturated carboxylic monoacid, $C_4$–$C_6$-α,β-ethylenically unsaturated carboxylic diacid, monoesters and monoamides of such carboxylic diacid.

11. The process of claim 10, wherein the hydrophobic functionality is provided by a constituent selected from the group consisting of $C_{10}$–$C_{22}$-acrylate, $C_{10}$–$C_{22}$-methacrylate, $C_{10}$–$C_{22}$-acrylamide, $C_{10}$–$C_{22}$-methacrylamide, $C_{10}$–$C_{22}$-vinyl ether, $C_{10}$–$C_{22}$-vinyl ester, siloxane, $C_{10}$–$C_{22}$-alpha olefin, fluorinated aliphatic sidechain of at least 6 carbons, styrene, and $C_1$–$C_{24}$-alkyl-substituted styrene.

12. The process of claim 11, wherein the hydrophobic functionality is provided by a constituent selected from the group consisting of $C_{12}$–$C_{22}$-acrylate, $C_{12}$–$C_{22}$-methacrylate, styrene, and $C_1$–$C_{24}$-alkyl-substituted styrene.

13. The process of claim 10, wherein the hydrophilic functionality is provided by a constituent selected from the group consisting of acrylic acid and methacrylic acid.

14. The process of claim 10, wherein the copolymer is selected from the group consisting of docosyl acrylate/styrene/acrylic acid and stearyl acrylate/methacrylic acid.

15. The process of claim 10, wherein the copolymer is present in an amount ranging from about 0.1 to about 12% by weight of the oil.

* * * * *